(12) United States Patent
Juan et al.

(10) Patent No.: US 10,959,720 B2
(45) Date of Patent: Mar. 30, 2021

(54) SYSTEM AND METHOD FOR SUTURE KNOT FORMING

(71) Applicant: Terumo Medical Corporation, Somerset, NJ (US)

(72) Inventors: Chun-Chia Juan, Taipei (TW); Yu-Shih Weng, Taipei (TW); Shu-Ling Cheng, Taipei (TW)

(73) Assignee: Terumo Medical Corporation, Somerset, NJ (US)

( * ) Notice: Subject to any disclaimer, the term of this patent is extended or adjusted under 35 U.S.C. 154(b) by 310 days.

(21) Appl. No.: 15/298,598

(22) Filed: Oct. 20, 2016

(65) Prior Publication Data

US 2017/0112492 A1 Apr. 27, 2017

Related U.S. Application Data

(60) Provisional application No. 62/332,701, filed on May 6, 2016, provisional application No. 62/245,841, filed on Oct. 23, 2015.

(51) Int. Cl.
*A61B 17/04* (2006.01)
*A61B 17/00* (2006.01)

(52) U.S. Cl.
CPC ...... *A61B 17/0487* (2013.01); *A61B 17/0057* (2013.01); *A61B 17/0469* (2013.01);
(Continued)

(58) Field of Classification Search
CPC ........ A61B 17/0469; A61B 2017/0474; A61B 17/0483; A61B 17/12009; A61B 17/0485; A61B 17/0475; A61B 2017/0477
See application file for complete search history.

(56) References Cited

U.S. PATENT DOCUMENTS 5,336,230 A * 8/1994 Leichtling .......... A61B 17/0469
128/898
5,797,928 A * 8/1998 Kogasaka .......... A61B 17/0469
606/139

(Continued)

FOREIGN PATENT DOCUMENTS

WO 2009/046443 A1 4/2009
WO 2014/141208 A1 9/2014

OTHER PUBLICATIONS

International Search Report for International Application No. PCT/US16/57857, dated Jan. 24, 2017.

(Continued)

*Primary Examiner* — Shaun L David
*Assistant Examiner* — Christina C Lauer
(74) *Attorney, Agent, or Firm* — Dergosits & Noah LLP; Todd A. Noah

(57) ABSTRACT

A knot may be formed in suture material using a device having an elongated body with a longitudinal axis and a holder. A rail portion of the suture material is secured with a first grasper on the elongated body and a non-rail portion of the suture material is secured with a second grasper on the holder. A plurality of helical windings may be created with the non-rail portion. Detaching the holder from the elongated body in a motion away from the longitudinal axis of the elongated body completes the knot. The holder may be wrapped around the elongated body in a knot-forming pattern.

21 Claims, 15 Drawing Sheets

(52) U.S. Cl.
CPC ...... *A61B 17/0482* (2013.01); *A61B 17/0483* (2013.01); *A61B 2017/0474* (2013.01); *A61B 2017/0475* (2013.01)

(56) References Cited

U.S. PATENT DOCUMENTS

| | | | | |
|---|---|---|---|---|
| 5,993,467 | A | 11/1999 | Yoon | |
| 6,171,317 | B1 * | 1/2001 | Jackson | A61B 17/0469 289/17 |
| 10,405,853 | B2 * | 9/2019 | Peter | A61B 17/0401 |
| 2005/0228406 | A1 * | 10/2005 | Bose | A61B 17/0469 606/144 |
| 2006/0206119 | A1 * | 9/2006 | Chu | A61B 17/0469 606/144 |
| 2007/0038229 | A1 | 2/2007 | de la Torre et al. | |
| 2011/0106078 | A1 | 5/2011 | Mueller | |
| 2014/0236188 | A1 | 8/2014 | Mehl et al. | |
| 2015/0008091 | A1 | 3/2015 | Koogle et al. | |
| 2015/0080917 | A1 | 3/2015 | Koogle, Jr. et al. | |

OTHER PUBLICATIONS

Written Opinion of the International Searching Authority for PCT/US16/57857, dated Jan. 24, 2017.
European Search Report and Written Opinion for European Patent Application No. 16858197.3; dated Jun. 5, 2019.
Office Action in Chinese Patent Application No. 201680075664.1, dated Aug. 4, 2020.

* cited by examiner

SYSTEM AND METHOD FOR SUTURE KNOT FORMING

RELATED APPLICATIONS

This application claims the benefit of U.S. Provisional Patent Application No. 62/245,841, filed Oct. 23, 2015 and U.S. Provisional Patent Application No. 62/332,701, filed May 6, 2016, the contents of which are incorporated by reference in their entirety.

FIELD OF THE PRESENT DISCLOSURE

The present disclosure relates generally to devices and methods for use in forming knots in suture material. In particular, techniques are disclosed for knot tying that may be used to close a puncture or opening associated with a percutaneous surgery.

BACKGROUND

Techniques have been developed to allow an increasing number and variety of procedures to be performed percutaneously, as a minimally invasive alternatives to conventional "open" surgeries that provide the benefits of reducing postoperative pain, decreasing hospital stays and periods of disability, and lowering costs for both hospitals and patients. Generally, these procedures utilize one or more elongated instruments that are introduced through a patient's skin for use in carrying out the procedure. For example, access to the patient's vasculature may be obtained by creating an opening in a suitable artery or vein.

However, in order to accommodate the instruments used during a percutaneous procedure, the openings may have relatively large diameters, such as 10 mm or larger. Correspondingly, it is desirable to attempt repair or otherwise provide support for the surrounding tissue during the postoperative healing process. Closing the openings formed to carry out the percutaneous procedure with sutures may reduce recovery time, minimize the risk of infection or provide other benefits. Although other methods of closing wounds have been developed, including the use of staples and clips, suturing remains a beneficial technique that provides advantages over these alternatives. Since tying knots in suture material typically requires a high level of surgical skill, particularly for intracorporeal knots, there is a need for systems and methods that may be used in an endoscopic context or in other situations in which a suture is to be placed within a patient's body. In particular, there is a need for techniques that increase the speed and reliability with which knots are formed and placed. As will be described in the materials below, the systems and methods of this disclosure satisfy these and other needs.

SUMMARY

This disclosure includes a device for forming a knot in suture material having an elongated body with a longitudinal axis and a first grasper configured to releasably secure suture material and a holder having a second grasper configured to releasably secure suture material, wherein the holder is detachably coupled to the elongated body and releases when moved in a motion away from the longitudinal axis.

In one aspect, the elongated body may have a guide at a distal end to slidably receive suture material.

In one aspect, the holder may be detachably coupled to the elongated body distally of the first grasper. Alternatively, the holder may be detachably coupled to the elongated body proximally of the first grasper.

In one aspect, a tab carrying the second grasper may be detachably coupled to the holder.

In one aspect, the holder may have a projecting portion aligned with the longitudinal axis of the elongated body that extends proximally from a location at which the holder is detachably coupled to the elongated body.

In one aspect, a rotating drum may be coaxially disposed over the elongated body. The drum may have a third grasper and rotation of the drum may be controlled by an actuator.

In one aspect, the holder may be wrapped around the elongated body in a knot-forming pattern with the second grasper at one end. A rotating drum may be coaxially disposed over the elongated body such that the holder is wrapped around the drum. The drum may have a detachable tab that releasably secures an end of the holder opposing the second grasper.

In one aspect, an organizer may be disposed adjacent to the holder in a knot-forming pattern. The organizer may be longitudinally aligned with the elongated body and extend distally over at least a portion of the wraps of the holder. A rotating drum may be coaxially disposed over the elongated body that is coupled to an actuator.

In one aspect, a tensioner may be looped around a portion of the holder.

In one aspect, a tab that may be detachably coupled to the knot forming device that releasably secures an end of the holder opposing the second grasper. The tab may have a projecting grasper that extends in a distal direction through the second grasper.

In one aspect, a trapper may be detachably coupled to the device such that the trapper secures suture material when detached. The trapper may also secure the second grasper to the suture material when detached.

In one aspect, the device may have a plurality of knot modules, such that each knot module has an elongated body with a holder wrapped around the elongated body in a knot-forming pattern.

This disclosure also includes a method for forming a knot in suture material. The method may involve providing a device having an elongated body with a longitudinal axis and a holder, releasably securing a rail portion of the suture material with a first grasper on the elongated body, releasably securing a non-rail portion of the suture material with a second grasper on the holder, creating a plurality of helical windings with the non-rail portion and detaching the holder from the elongated body in a motion away from the longitudinal axis of the elongated body to complete the knot.

In one aspect, the plurality of helical windings may be created over the rail portion. Alternatively, the plurality of helical windings may be created and then slid distally over the rail portion.

In one aspect, the elongated body may be coaxially disposed within a rotating drum and the plurality of helical windings may be created by driving rotation of the drum.

In one aspect, the holder may be wrapped around the elongated body in a knot-forming pattern with the second grasper at one end and creating the plurality of helical windings may involve withdrawing the holder to pull the non-rail portion into the knot-forming pattern.

In one aspect, an actuator may be slid distally along the longitudinal axis of the elongated body to position the created plurality of helical windings over the rail portion.

In one aspect, a tensioner may be looped around a portion of the holder.

In one aspect, withdrawing the holder may involve detaching a tab from the device such that the tab is attached to an end of the holder opposing the second grasper.

In one aspect, a trapper coupled to the device may secure the non-rail portion when detached.

In one aspect, the device may have a plurality of knot modules, such that each knot module has an elongated body with a holder wrapped around the elongated body in a knot-forming pattern. Correspondingly, the method may involve forming a knot with each knot module.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

(FIG. 12 shows twice)

DETAILED DESCRIPTION

Figure 1:
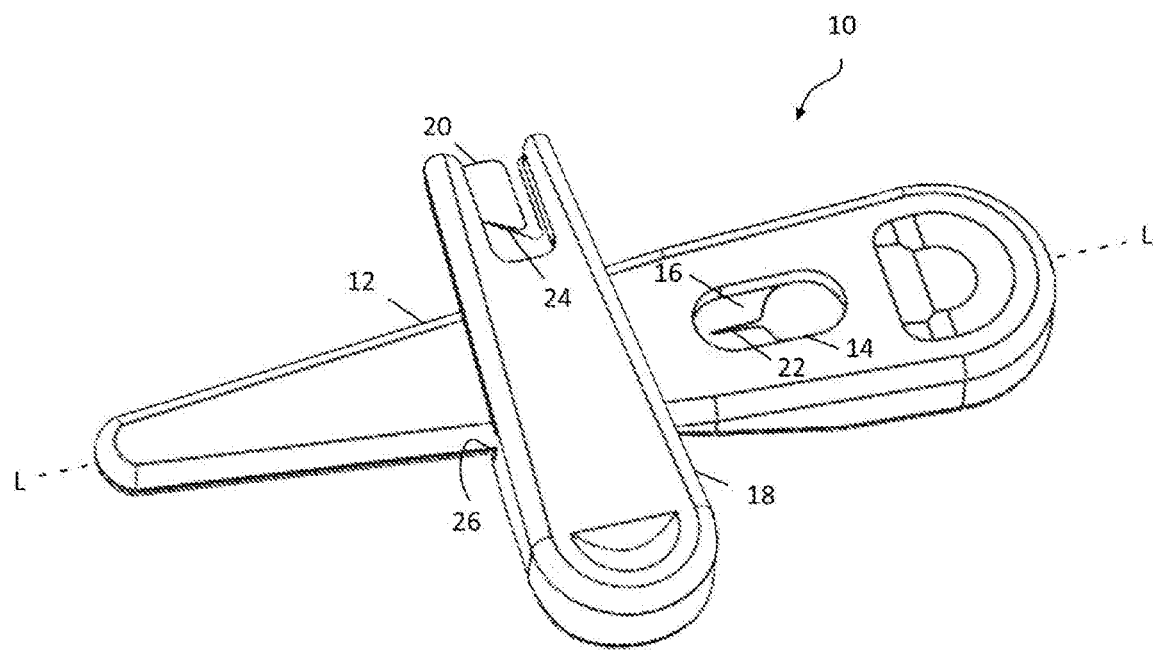
FIG. 1 depicts a schematic view of an embodiment of a knot forming device having a grasper in an aperture of the elongated body.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. Notably, aspects of this disclosure are described in the context of an endoscopic procedure. However, different terms may be employed for procedures depending on the location of interest. As illustrations, endoscopy may refer to visualization of the digestive tract, colonoscopy may refer to visualization of the colon, arthroscopy may refer to visualization of a joint, laparoscopy may refer to visualization of the anatomy within the abdomen, thoracoscopy may refer to visualization of the anatomy within the chest, urethroscopy may refer to visualization of the urinary tract, bronchoscopy may refer to visualization of the respiratory tract, and other terms may be used depending on where the procedure is performed. It should be appreciated that the techniques of this disclosure may be applied in conjunction with any procedure involving the placing of a suture knot within the interior of a patient's body.

Finally, as used in this specification and the appended claims, the singular forms "a, "an" and "the" include plural referents unless the content clearly dictates otherwise.

Referring to FIG. 1, a knot forming device 10 according to one embodiment is shown. As depicted, knot forming device 10 includes an elongated body 12 having an aperture 14 integrated into the body that carries a first grasper 16. A holder 18 is detachably coupled to elongated body 12 and includes a second grasper 20. Graspers 16 and 20 are configured to releasable engage suture material and may be implemented in any suitable form. In this embodiment, the first grasper 16 may be constructed from a relatively thin sheet of metal having a tapering slot 22 that narrows from a dimension greater than the diameter of the suture material to a dimension that is less, so that movement of the suture into the narrowed dimension causes it to be frictionally engaged. Correspondingly, the suture may be released by returning it an area of slot 22 having a greater dimension. Similarly, the second grasper 20 may also be formed from a metal sheet with a tapering slot 24. It will be appreciated that either or both of graspers 16 and 20 may also be formed from plastic, rubber or other material offering suitable friction and may employ clips, clamps or any other mechanism for releasably securing suture material.

As shown, elongated body 12 generally defines a longitudinal axis indicated by the line L-L. In this embodiment, elongated body 12 tapers from a proximal end to a distal end along the longitudinal axis, although other configurations may be employed as described below. Holder 18 may be coupled to elongated body 12 in any suitable manner, such as by having a recess 26 that frictionally engages at least a portion of elongated body 12, although any releasable connection may be employed. Correspondingly, holder 18 may be detached from elongated body 12 by movement in a motion away from the longitudinal axis of elongated body 12, for example a perpendicular motion or other suitable angle.

Figure 2:
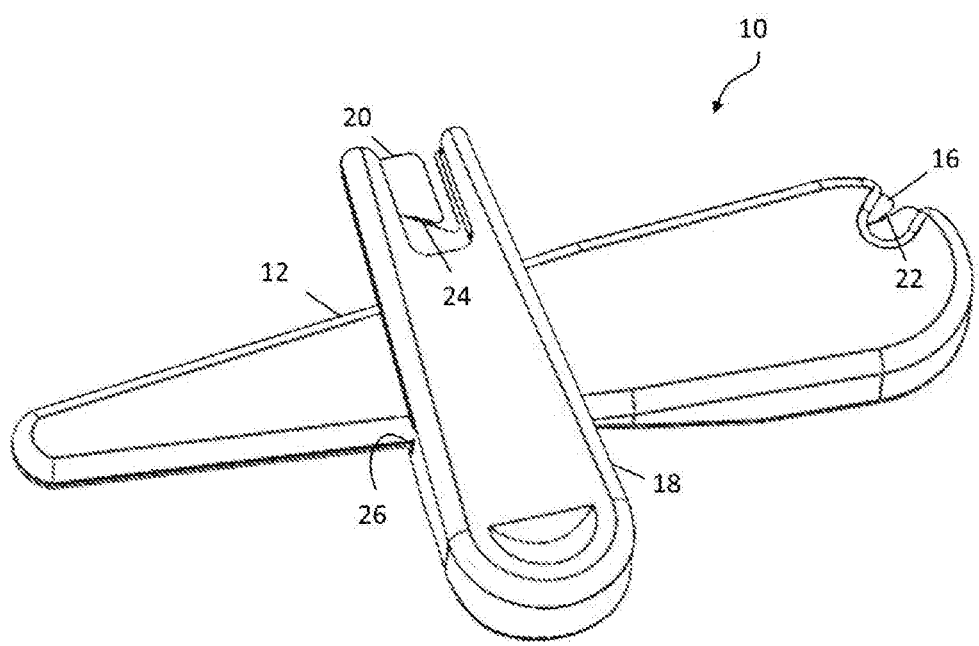
FIG. 2 depicts a schematic view of an embodiment of a knot forming device having a grasper on the perimeter of the elongated body.
Figure 3:
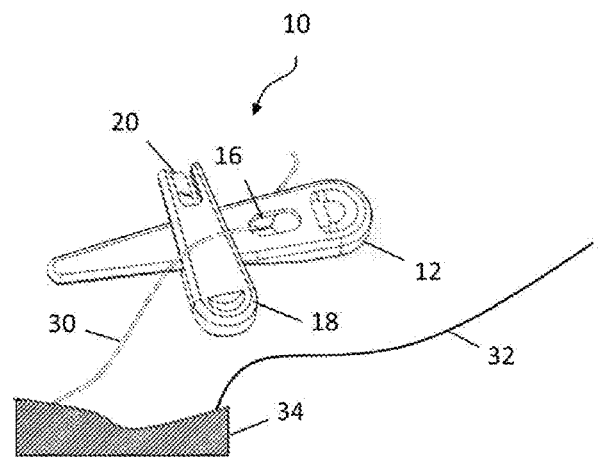
FIGS. 3-5 schematically depict a sequence of operations in forming a knot with an embodiment of a knot forming device.

A similar alternative embodiment is shown in FIG. 2, in which the first grasper 16 is positioned at a perimeter of elongated body 12, rather than in an aperture. As such, the first grasper 16 may capture a suture without the need to first thread the suture through an opening.

In use, knot forming device 10 facilitates creating and placing a knot in suture material. Typically, suture material is passed through tissue that is sought to be joined or supported with a needle or the like. Correspondingly, the suture material in which the knot is to be formed may include a "rail" portion and a "non-rail" portion. A knot may be formed by wrapping several helical turns of the non-rail portion around the rail portion. The knot is tightened and placed by sliding the loops of the non-rail portion along the rail end until they abut the tissue being sutured. By pulling the suture material, the loops constrict about the rail portion and are held in place by friction.

Figure 4:
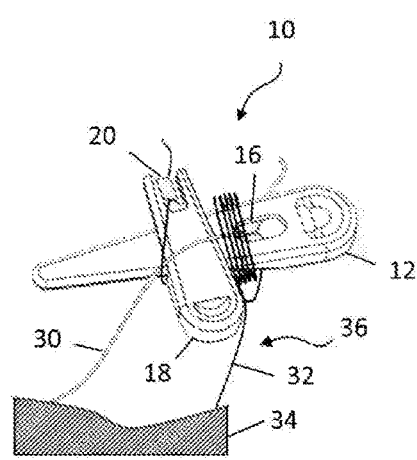
Figure 5:
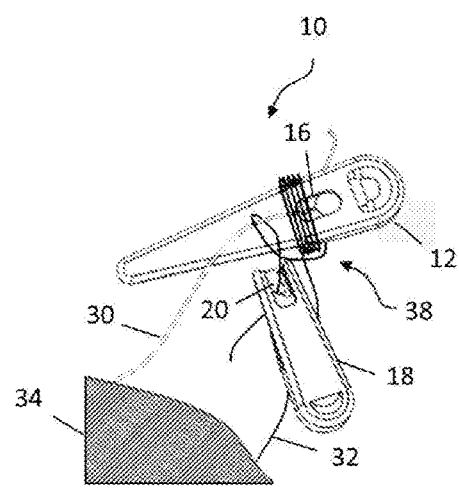
Figure 6:
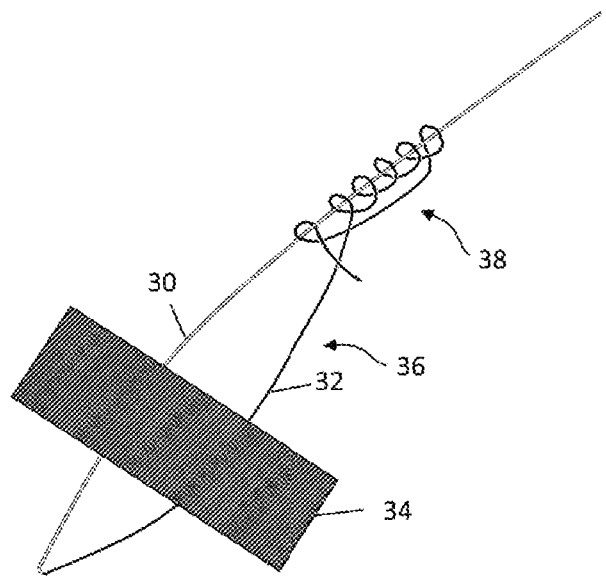
FIG. 6 schematically depicts a knot formed according to FIGS. 3-5.

These aspects of the disclosure are schematically illustrated in FIGS. 3-6. Beginning with FIG. 3, the rail portion 30 of the suture has been captured by the first grasper 16 of elongated body 12. The non-rail portion 32 represents the other end of the suture, having been passed through tissue 34. Although rail portion 30 is depicted in outline and non-rail end is depicted as solid to help distinguish them, it should be appreciated that both portions are part of the same suture. In this embodiment of knot forming device 10, the first grasper 16 is positioned relatively proximal to holder 18 along elongated body 12. As such, rail portion 30 passes over holder 18 before being retained by the first grasper 16. Next, as indicated in FIG. 4, non-rail portion 32 is helically wrapped around elongated body 12 and rail portion 30, forming a first loop 36. The wraps are formed proximally to holder 18 as shown. The number of turns employed may vary as warranted by the application, but should be a number sufficient to create the desired friction when the knot is placed and tightened. As an example only, and without limitation, five wraps may be made. Following the helical wraps, non-rail portion 32 is then passed under holder 18 and over rail portion 30 before being secured by the second grasper 20. Formation of the knot may be completed by detaching holder 18 and moving it in a radial direction away from the longitudinal axis of elongated body 12 as indicated in FIG. 5. Since non-rail portion 32 is secured by the second grasper 20, this pulls the non-rail portion 32 under rail portion 30 and over the free portion of non-rail portion 32, creating a half-hitch around rail portion 30 to form a second loop 38. The resulting knot may be slid off elongated body 12 in the distal direction, elongated body 12 may be withdrawn in the proximal direction to leave the loops and helical turns in place, or a combination of such motions may be used to free the knot from knot forming device 10. The knot formed according to these aspects of the disclosure is schematically illustrated in FIG. 6. Correspondingly, the helical turns, first loop 36 and second loop 38 may then be pushed along rail portion 30 to place and tighten the knot against tissue at a desired position within the patient.

Figure 7:
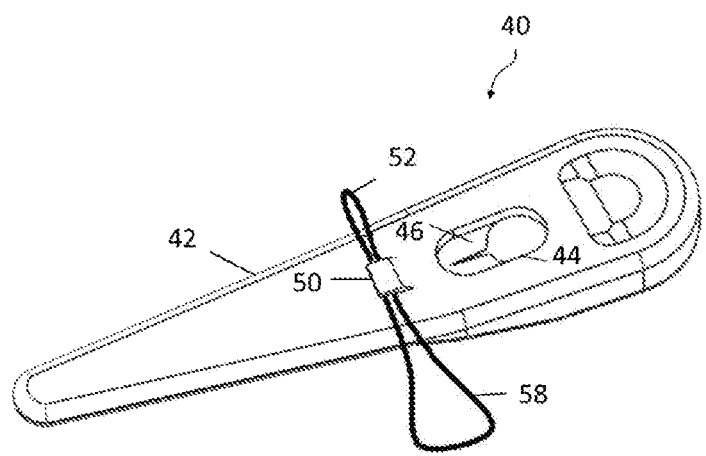
FIG. 7 depicts a schematic view of an embodiment of a knot forming device having a wire loop holder.

Another embodiment of this disclosure is the knot forming device 40 shown in FIG. 7. As in the previous embodiments, elongated body 42 may have an aperture 44 with first grasper 46. However, in this embodiment holder 58 may be configured as a loop formed from wire or other similar material. Holder 58 is coupled to elongated body 42 by clip 50. One end of the loop of holder 58 forms second grasper 52. Although the second grasper 52 may not engage suture material as securely as the embodiments described above, second grasper 52 may still be used to draw the suture material through the wraps and loops formed around elongated body 42, particularly if the free end of the suture material is held or otherwise retained. As such, the use of knot forming device 40 may follow the techniques described above.

Figure 8:
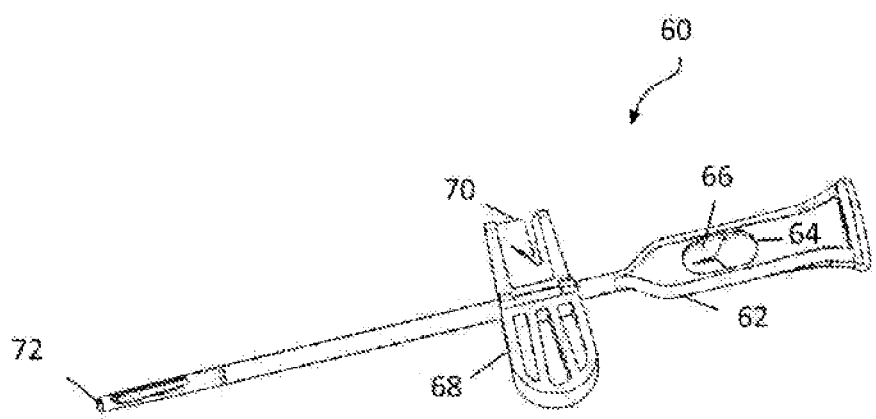
FIG. 8 depicts a schematic view of an embodiment of a knot forming device having a guide at a distal end of the elongated body.

In another aspect, knot forming device 60 is an alternative embodiment shown in FIG. 8. Again, in a similar manner to that described above, elongated body 62 may have an aperture 64 with first grasper 66. Here, elongated body 62 has a proximal portion with first grasper 66 and a distal portion that is configured as a thin cylinder to which detachable holder 68 with second grasper 70 may be coupled. In this embodiment, holder 68 may be configured to snap fit over the cylindrical portion, distal to the first grasper 66. Elongated body 62 may also feature a guide 72 at the distal end. The suture material, such as the rail portion may be threaded through guide 72 or otherwise captured. Guide 72 may be formed from a port in the end of elongated body 72 that communicates with a port in the sidewall to provide a relatively straight path of travel for the suture material. It is to be appreciated that other structures may be employed for guide 72 to achieve substantially equivalent function, such as a channel, a slot, a groove or the like. Together, guide 72 and the retention of the suture in first grasper 66 help keep the rail end of the suture aligned with the longitudinal axis of elongated body 62, facilitating the helical wrapping of the non-rail portion.

Use of knot forming device 60 is substantially the same as described above with respect to knot forming devices 10 and 40 and may be used to create a knot of the same configuration. Further, once the formed loops and wraps of the knot have been slid distally off elongated body 62, the knot may be tightened slightly to resist being pushed back over elongated body 62. Under these conditions, elongated body 62 may now be used to push the knot towards the tissue being secured to help place the knot in its desired location. Guide 72 may also be used to help cinch the knot more tightly by resisting when the rail portion is tensioned, which in turn helps remove any slack suture material.

Figure 9:
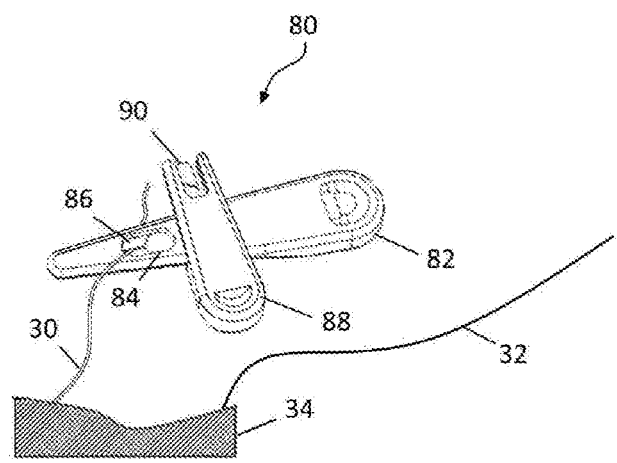
FIGS. 9-11 schematically depict a sequence of operations in forming another knot with an embodiment of a knot forming device.
Figure 10:
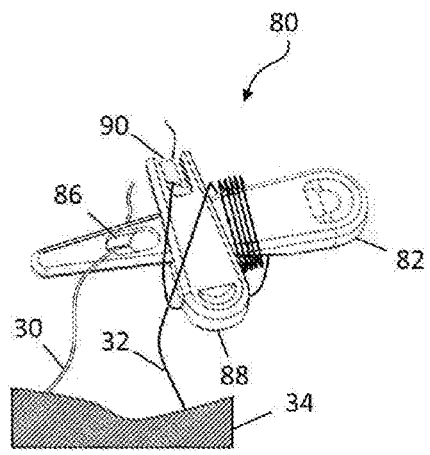
Figure 11:
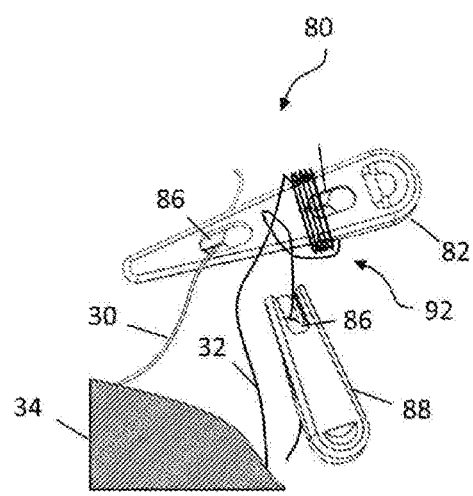

As will be appreciated, altering the configuration in the relationship between the first grasper of the elongated body and the second grasper of the detachable holder may allow the formation of different knots. For example, FIGS. 9-11 show an embodiment in which knot forming device 80 again may include elongated body 82 having an aperture 84 with first grasper 86. In this embodiment, detachable holder 88 with second grasper 90 may be coupled to elongated body 82 at a position that is proximal to the first grasper 86.

Figure 12:
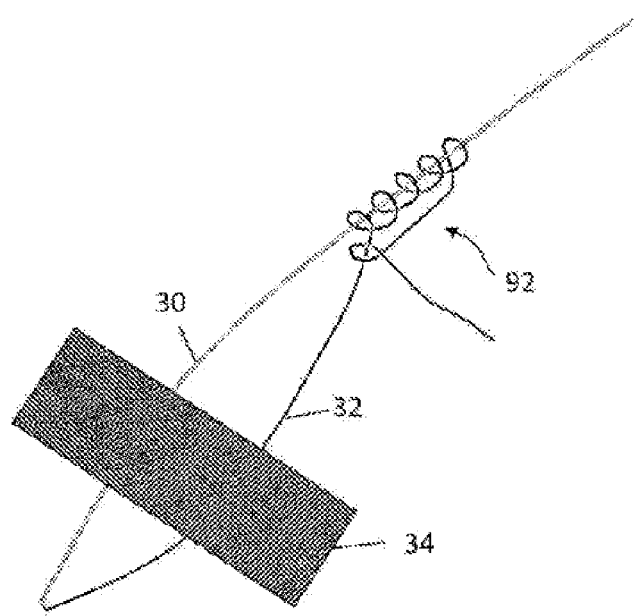
FIG. 12 schematically depicts a knot formed according to FIGS. 9-11.

As shown in FIG. 9, a knot may be formed by securing the rail portion 30 of the suture with the first grasper 86 of elongated body 82. Next, non-rail portion 32 may be passed over holder 88 and then helically wrapped around elongated body 82. The wraps are formed on the proximal side of holder 88 and any suitable number of turns may be employed as described above. Following the helical wraps, non-rail portion 32 is then passed under holder 88 and over the portion of non-rail portion 32 that extends from the tissue 34 to the helical wraps before being secured by the second grasper 90 as shown in FIG. 10. Formation of the knot may be completed by detaching holder 88 and moving it in a radial direction away from the longitudinal axis of elongated body 12 as indicated in FIG. 11. Since non-rail portion 32 is secured by the second grasper 90, this pulls the non-rail portion 32 under the portion of non-rail portion 32 extending from the tissue, creating a half-hitch to form a self-loop 92. Relative movement of the resulting knot distally along elongated body 82 slides the helical wraps over rail portion 30, which is being retained by the first grasper 86. The knot formed according to these aspects of the disclosure is schematically illustrated in FIG. 12. Similar to the procedures described above, the helical turns and self-loop 92 may then be pushed along rail portion 30 to place and tighten the knot against tissue at a desired position within the patient. These steps may also be used with the other knot forming device configurations of this disclosure.

Figure 13:
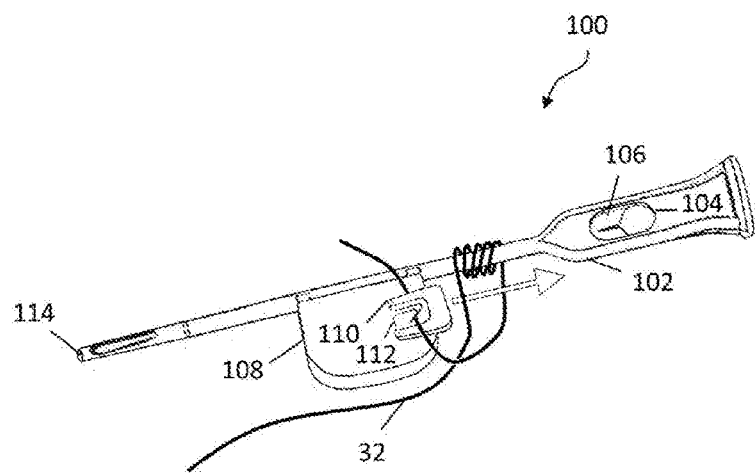
FIG. 13 depicts a schematic view of an embodiment of a knot forming device having a detachable tab on the holder.

Another embodiment that may be used to tie the knot shown in FIG. 12 is the knot forming device 100 depicted in FIG. 13. As shown, knot forming device 100 features elongated body 102 having an aperture 104 with first grasper 106. In this embodiment, detachable holder 108 has a separately detachable tab 110 that carries second grasper 112. A guide 114 may be provided at the distal end of elongated body 102 as described above. Although the first grasper 106 is shown to be proximal to the second grasper 112, in alternative embodiments the first grasper 106 may be distal relative to the second grasper 112 if desired. For clarity, this figure depicts only non-rail portion 32. As indicated, non-rail portion 32 may be helically wrapped around elongated body 102, passed over the portion of non-rail portion 32 that extends from the patient's tissue before and then secured by the second grasper 112 of tab 110. Withdrawing tab 110 under the portion of non-rail portion 32 extending from the tissue as indicated by the arrow creates a half-hitch to form a self-loop in a manner similar to that described with respect to FIG. 11. Holder 108 may then be detached from elongated body 102 and the formed knot may be placed and tightened using any of the techniques described above. It is to be appreciated that a knot having the configuration shown in FIG. 12 may be formed either by first securing the rail portion of the suture in first grasper 106 so that the helical wraps are formed around the rail portion or by using a distally-positioned second grasper 112 (in alternative embodiments of knot forming device 100), in which the helical wraps and self-loop are created first and then slid over the retained rail portion. Moreover, since the configuration in the embodiment of FIG. 13 positions first grasper 106 relatively proximal of second grasper 112, appropriate manipulation of the non-rail portion relative to the rail portion retained in first grasper 106 allows formation of the knot shown in FIG. 6 as well.

Figure 14:
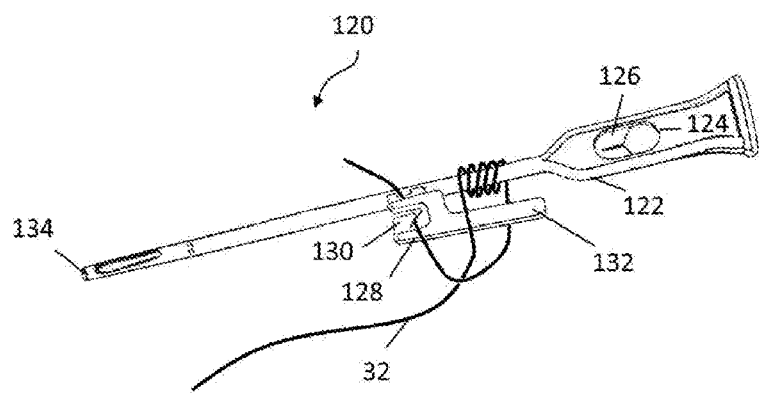
FIG. 14 depicts a schematic view of an embodiment of a knot forming device having a holder with a grip.

Various modifications may be made to the configuration of the holder as an alternative to having a detachable tab. For example, FIG. 14 shows an embodiment of knot forming device 120 including elongated body 122 having an aperture 124 with first grasper 126. Holder 128 is detachably coupled to elongated body 122 in any suitable manner, such as a snap fit attachment. Holder 128 has a second grasper 130 and a projecting grip 132. A guide 134 may be provided at the distal end of elongated body 122 as described above. Again, this figure depicts only non-rail portion 32 for clarity. Non-rail portion 32 may be helically wrapped around elongated body 122 and passed over the portion of non-rail portion 32 before being secured by second grasper 130. As shown, this allows grip 132 to extend proximally past the helical windings, between the strands of non-rail portion 32. Consequently, detaching holder 128 pulls the secured end of non-rail portion 32 under the non-rail portion 32 extending from the tissue to create a half-hitch and form a self-loop as noted above.

Figure 15:
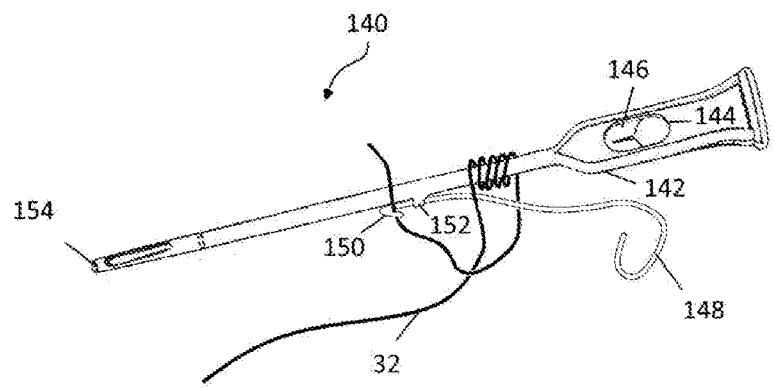
FIG. 15 depicts a schematic view of an embodiment of a knot forming device having a holder with a wire hook.

As another example, FIG. 15 shows an embodiment of knot forming device 140 including elongated body 142 having an aperture 144 with first grasper 146. Holder 148 is configured as a pulling wire, with second grasper 150 formed by a hook end. Holder 148 may be detachably coupled to elongated body 142 in any suitable manner, such as with clip 152. In other embodiments, holder 148 may have other configurations, such as being formed from a wire loop similar to holder 58 as depicted in FIG. 7, but oriented to be generally aligned with the longitudinal axis of elongated body 142. A guide 154 may be provided at the distal end of elongated body 142 as described above. Once more, this figure depicts only non-rail portion 32 for clarity. Non-rail portion 32 may be helically wrapped around elongated body 142 and passed over the non-rail portion 32 extending from the patient's tissue before being secured by second grasper 150. In turn, this the end of holder 148 opposing second grasper 150 to extend proximally past the helical windings, between the strands of non-rail portion 32. Consequently, holder 148 may be detached and used to pull the secured end of non-rail portion 32 under the non-rail portion 32 extending from the tissue to create a half-hitch and form a self-loop as in the above embodiments.

Figure 16:
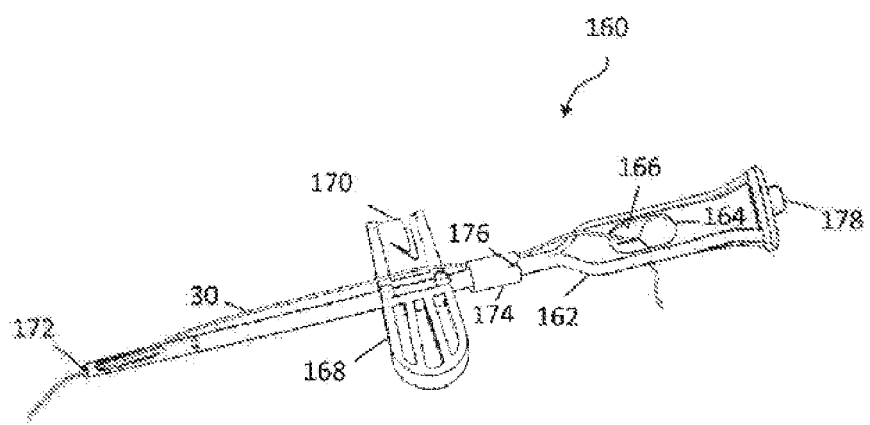
FIG. 16 depicts a schematic view of an embodiment of a knot forming device having a driven rotating drum.

In yet another aspect, the knot forming devices of this disclosure may feature mechanisms to facilitate the formation of helical wraps of the non-rail portion of the suture material. One suitable embodiment is shown in FIG. 16 with respect to knot forming device 160. As in the previous embodiments, elongated body 162 may have an aperture 164 with first grasper 166. Elongated body 162 has a proximal portion with first grasper 166 and a distal portion that is configured as a thin cylinder to which detachable holder 168 with second grasper 170 may be coupled. In this embodiment, holder 168 may be configured to snap fit over the cylindrical portion, distal to first grasper 166, but any releasable means of attachment may be employed. Elongated body 162 may also feature a guide 172 at the distal end.

A rotating drum 174 is coaxially disposed over the cylindrical portion of elongated body 162, positioned proximal to holder 168. As shown, rail portion 30 of the suture material may be threaded through guide 172, over holder 168 and through drum 174 before being retained by first grasper 166. Correspondingly, the end of non-rail portion 32 (not shown in this view) may be releasably secured by grasper 176 on drum 174. Drum 174 may be configured to rotate on the cylindrical portion of elongated body 162 a number of times corresponding to the number of helical wraps of the non-rail portion 32 desired when forming a knot. Any suitable driving mechanism may be employed, such as spring driven or electrical motor driven. Elongated body 162 may also have an actuator 178 for controlling rotation of drum 174. Actuator 178 is coupled mechanically or electrically as warranted so that actuation causes rotation of drum 174 a desired number of rotations about the cylindrical portion of elongated body 162. Therefore, the end of non-rail portion 32 may be captured in grasper 176 and actuator 178 may be controlled to rotate drum 174 to cause the formation of helical wraps of non-rail portion 32. Pursuant to the above discussion, knots similar to those depicted in FIGS. 6 and 12 may be formed using such driven helical winding of the non-rail portion 32. As also described above, when forming knots having the configuration shown in FIG. 12, rail portion 30 may or may not be threaded through drum 174, as the helical windings and self-loop of the non-rail portion 32 may be formed either over the rail portion 30 or may be slid over the rail portion 30 after formation.

Figure 17:
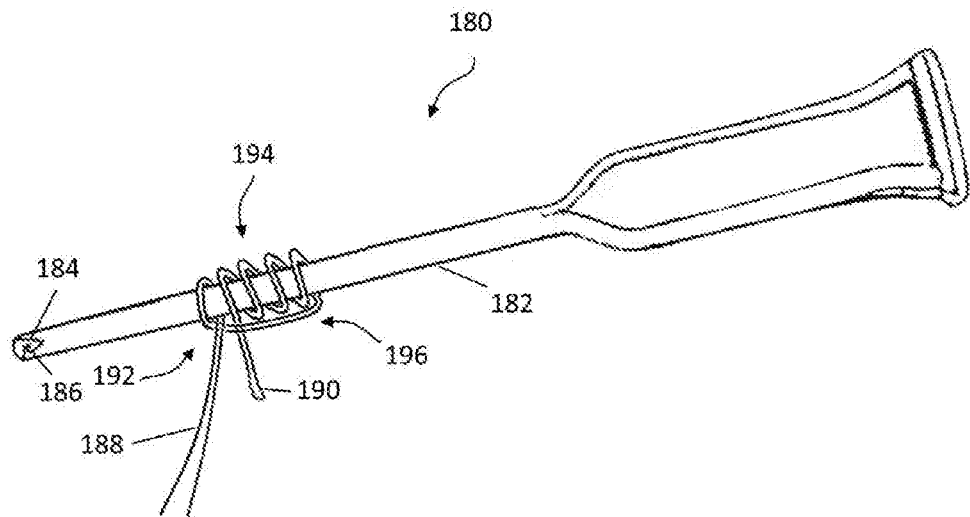
FIG. 17 depicts a schematic view of an embodiment of a knot forming device having a holder wrapped in a knot-forming pattern.

Another embodiment of this disclosure that facilitates formation of helical windings in the non-rail portion of the suture material is depicted in FIG. 17 with respect to knot forming device 180. This embodiment includes an elongated body 182 having a first grasper 184 positioned at the distal end. The first grasper 184 may include a tapering slot 186 similar to the embodiments described above that is dimensioned to receive and releasably secure suture material, such as rail portion 30 (not shown in this view for clarity). Knot forming device 180 also features holder 188 that is detachably coupled to elongated body 182. As shown, holder 188 may be configured as a doubled length of suitably malleable wire material and may be formed from an appropriate metal, including shape memory materials (e.g., nickel titanium alloys), polymers or others. At the point the wire doubles back, the resulting loop forms second grasper 190, which may be used to releasably secure suture material as described above. Holder 188 is secured by being wound around a circumference of elongated body 182 in a desired pattern that will form a knot when replaced by suture material, such as non-rail portion 32 (also not shown in this view for the sake of clarity). In this embodiment, the pattern creates a knot having the characteristics shown in FIG. 6. For example, holder 188 may be used to create a half hitch 192 at a relatively distal position and then a series of helical windings 194 may be made in a proximal to distal direction. Finally, the end of holder 188 with second grasper 190 may be fed under the loop 196 created by half hitch 192 to complete the pattern. As will be appreciated, other patterns may be employed to form knots having different characteristics. The number of helical windings may be adjusted as desired to tailor the amount of friction generated by the resulting knot.

In use, an end of rail portion 30 may be retained by grasper 184 and an end of non-rail portion 32 may be retained by second grasper 190. Correspondingly, pulling the end of holder 188 that is opposite second grasper 190 causes holder 188 to unwind from elongated body 182, drawing non-rail portion 32 on a path that retraces the winding pattern of holder 188. When holder 188 has been pulled in a radial direction away from the longitudinal axis of elongated body 182 and is completely disengaged, non-rail portion 32 will have replaced the pattern of holder 188, forming the helical wraps and loop described above with respect to FIG. 6. Therefore, the helical wraps may be slid distally off elongated body 182 and over rail portion 30. The knot may then be placed and tightened.

Figure 18:
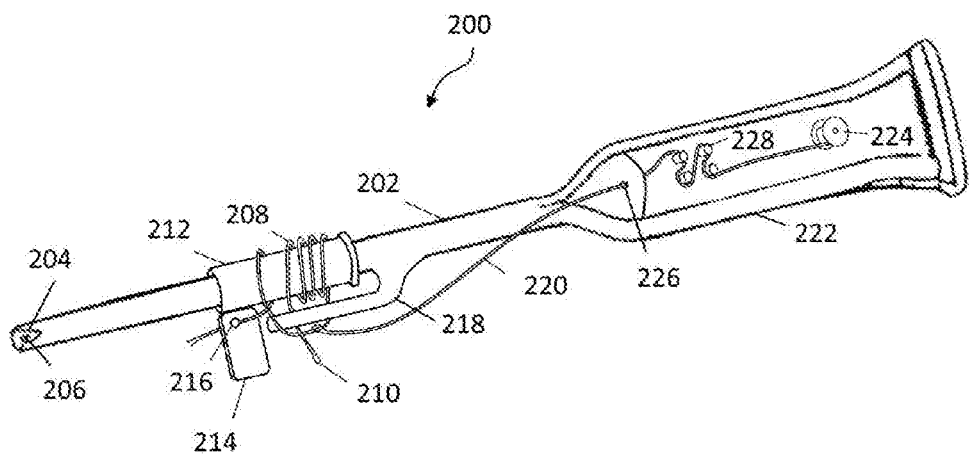
FIG. 18 depicts a schematic view of an embodiment of a knot forming device having a tensioner.

The general design of FIG. 17 may be enhanced with various modifications as desired. To help illustrate, another embodiment in the form of knot forming device 200 is shown in FIG. 18. This embodiment also includes an elongated body 202 having a first grasper 204 positioned at the distal end. The first grasper 204 may include a tapering slot 206 as noted above. Knot forming device 200 also features holder 208 having similar characteristics to holder 188 that is detachably coupled to elongated body 202. A second grasper 210 is located at one end of holder 208 to releasably secure suture material, such as non-rail portion 32 (not shown in this view for clarity). Holder 208 is secured by being wound around rotating drum 212, which is coaxially disposed over elongated body 202. As noted above, holder 208 may be wound in a desired pattern that will form a knot when replaced by suture material. A detachable tab 216 may be coupled to drum 212 and may include grasper 216 for releasably securing an end of holder 208 opposing second grasper 210.

Further, knot forming device 200 may also include an organizer 218 disposed adjacent to holder 208. Referring to FIG. 18, the organizer is attached to elongated body 202 at a location proximal to rotating drum 212 and extends longitudinally in the distal direction over at least a portion of drum 212 to contain the wraps of holder 208, helping to keep them from being entangled. Organizer 218 may be detachable or may be integral or otherwise permanently secured to elongated body 202.

In another aspect, knot forming device 200 may include tensioner 220, which may be a doubled string or other similar element that loops around a portion of holder 208 as shown. Excess material may be stored within a portion of handle 222 of elongated body 202, such as on spool 224, and may thread through opening 226. Tensioner 220 may be configured to impart a proximally oriented resistance to the knot after the suture has been pulled into the pattern dictated by holder 208. A suitable degree of resistance may be provided frictionally by winding the strands of tensioner 220 around posts 228 positioned within handle 222. The number of posts 228 and the pattern of winding may be adjusted as warranted. Alternatively or in addition, spool 224 may be provided with a clutch or other similar mechanism to resist rotation and provide the desired tension.

Use of knot forming device 200 generally follows the techniques described above. Rail portion 30 may be retained by first grasper 204 and non-rail portion 32 may be retained by second grasper 210. Tab 214 may then be detached from drum 212 and used to pull holder 208 free from elongated body 202. Drum 212 rotates during this operation to facilitate the unwinding of holder 208 and the resulting winding of non-rail portion 32. As noted above, organizer 218 maintains holder 208 in its desired configuration during the operation. Tensioner 220 may then help keep the helical windings and loop of non-rail portion 32 in their proper orientation after non-rail portion 32 has been pulled into the knot pattern and is slid distally over rail portion 30. As described above, tension may then be applied to rail portion 30, such as by withdrawing elongated body 202 in the proximal direction to pull the formed knot into the desired position.

Figure 19:
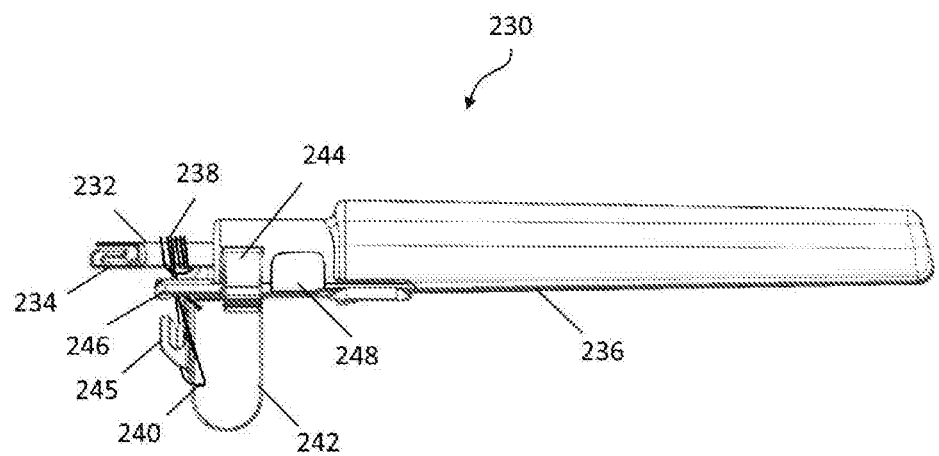
FIG. 19 depicts a schematic view of an embodiment of a knot forming device having a detachable tab that secures an end of the holder.
Figure 20:
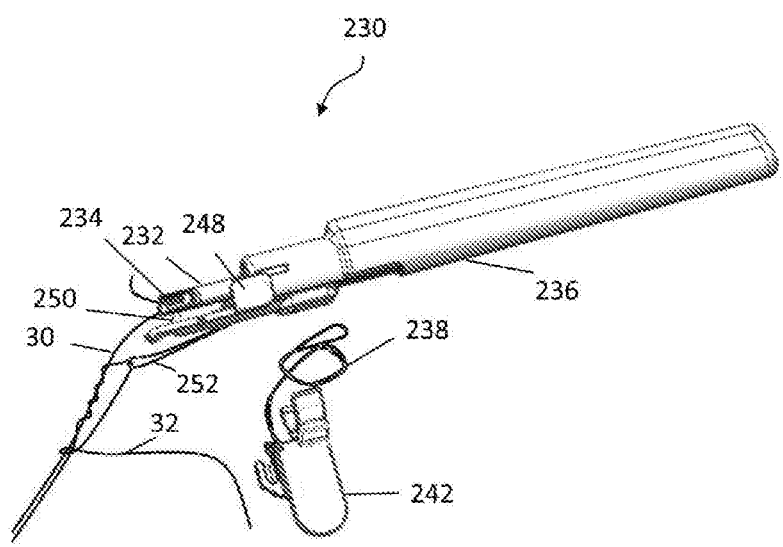
FIG. 20 depicts a schematic view of the embodiment of FIG. 19 with the tab detached.
Figure 21:
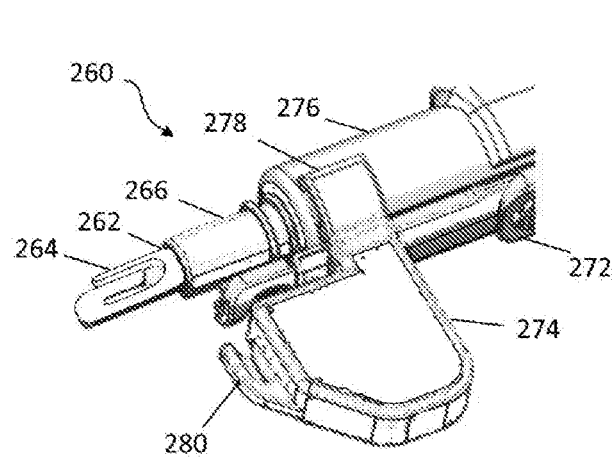
FIGS. 21-24 schematically depict an embodiment of a knot forming device with a trapper having a passageway.

In another aspect, the techniques of this disclosure may be adapted to facilitate the transfer of the helical wraps of the non-rail portion over the rail portion. As shown in FIG. 19, knot forming device 230 may have an elongated body 232 having a first grasper 234 positioned at the distal end. Elongated body 232 may extend from handle 236 as shown. Holder 238 may be detachably coupled to elongated body 232 as a doubled length of wire wound around a circumference of elongated body 232 in a desired knot-forming pattern as discussed above. The end of holder 238 opposing second grasper 240 may be secured to tab 242, which may be detachably coupled to knot forming device 230, such as by snap clip 244. Tab 242 may also feature a protruding grasper 245 that is configured to extend through grasper 240, formed by the loop of holder 238. As shown, knot forming device 230 also includes organizer 246 to provide a similar function to that described above. Actuator 248 is slidable along the longitudinal axis of elongated body 232. With actuator 248 in its proximal position, holder 238 may be used to draw suture material into a knot forming pattern pursuant to the techniques of this disclosure noted above. In one aspect, an end of non-rail portion 32 may be retained by grasper 245 which extends through second grasper 240 as discussed above. Correspondingly, detaching tab 242 automatically pulls non-rail portion 32 through second grasper 240 so that it may be retained and pulled into the knot pattern as holder 238 is withdrawn. After tab 242 has been detached and pulled away from elongated body 232, actuator 248 may be slid distally to push the helical wraps and loop formed in non-rail portion 32. This configuration is depicted in FIG. 20, showing that the helical wraps of non-rail portion 32 have been pushed over rail portion 30. As shown, actuator 248 may have a pusher 250 that extends in a generally perpendicular direction to the longitudinal axis of elongated body 232 in order to engage the helical wraps of non-rail portion 32. As will be appreciated, this configuration of an actuator 248, along with pusher 250 (if provided), may reduce or eliminate the need to manually push the wraps off of elongated body 232, allowing for a more automated procedure. In some embodiments, tab 242 may be configured to prevent operation of actuator 248 until detached. Further, knot forming device 230 may also include tensioner 252 that may be configured and operate as described above.

In additional embodiments, one or more structures may be provided to maintain the connection between the holder and the end of the non-rail portion of suture material. For example, FIGS. 21-24 schematically depict partial detail views of knot forming device 260, which features elongated body 262 having a first grasper 264 positioned at the distal end and rotating drum 266 for receiving holder 268 (not shown in FIGS. 21 and 22 for clarity), when wound into a knot-forming pattern as discussed above. Also similar to the above embodiments, actuator 272 is slidable along the longitudinal axis of elongated body 262. Tab 274 is detachably coupled to housing 276 by clip 278. Tab 274 may also include projecting grasper 280, which as described above is configured to extend through second grasper 282 of holder 268 when wound around drum 266.

Figure 22:
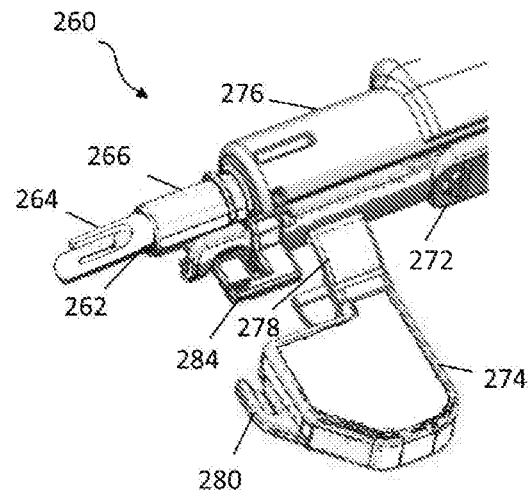
Figure 23:
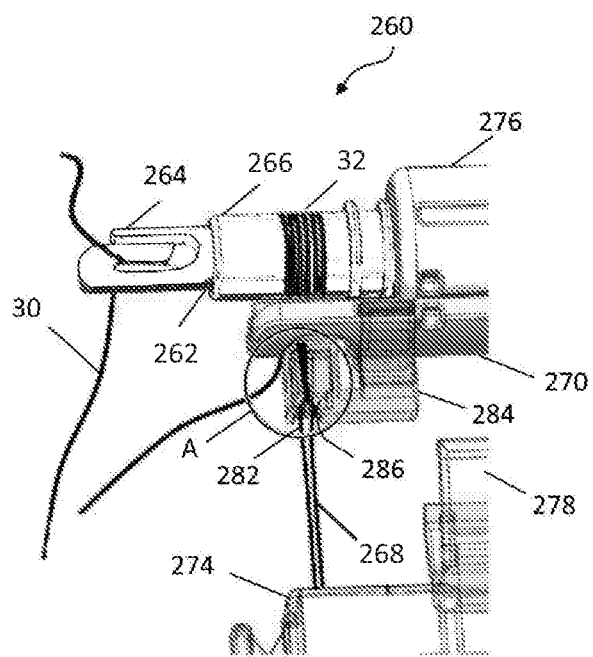
Figure 24:
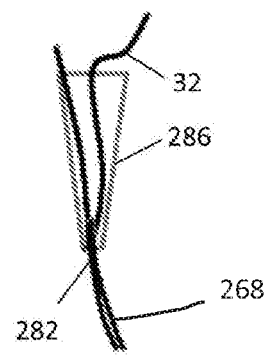
Figure 25:
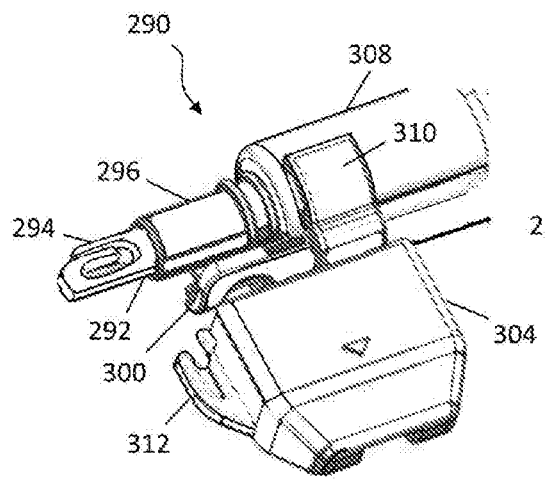
FIGS. 25-28 schematically depict an embodiment of a knot forming device with a trapper having a clip.
Figure 26:
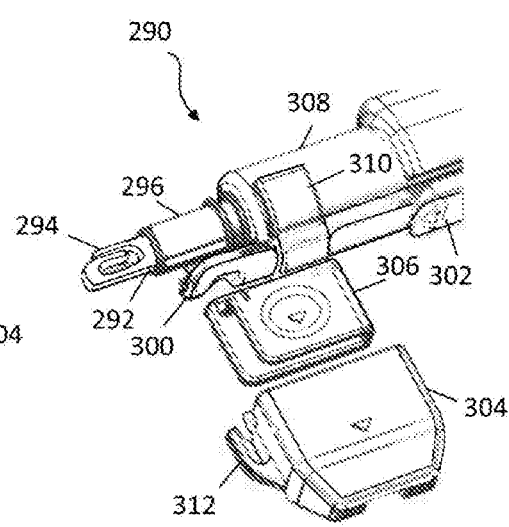
Figure 27:
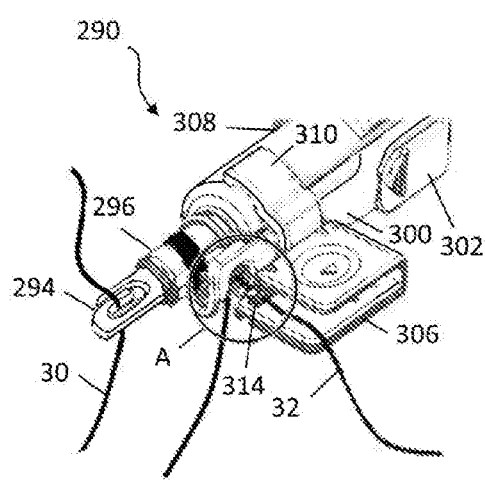

Another detachable element, trapper 284, is configured to clip onto actuator 272, coaxially between tab 274 and elongated body 262, as shown more clearly in FIG. 22, with tab 274 having been detached. Notably, in other embodiments, these elements, as well as others, may be releasably secured to other components of the knot forming device depending on the given configuration. For example, if an actuator 272 is not employed, the trapper 284 may clip to any suitable structure. In this embodiment, trapper 284 includes a tapering passageway 286, through which holder 268 is threaded in the starting configuration. As shown in FIG. 23, tab 274 has been detached and pulled away from the longitudinal axis of elongated body 262 to draw non-rail portion 32 of the suture around drum 266 in the desired pattern. Further, the end of rail portion 30 is shown to be releasably secured by first grasper 264 of elongated body 262. The dimensions of passageway 286 allow free travel of holder 268 alone, but tapers with distance from elongated body 262. Correspondingly, the output of passageway 286 has a sufficiently reduced dimension to prevent travel of second grasper 282 when non-rail portion 32 is being retained. To illustrate this aspect more clearly, a further detail of area A in FIG. 23 is schematically depicted in FIG. 24. As indicated, the combined second grasper 282 and non-rail portion 32 jams at the output of passageway 286, maintaining their engagement. Since travel of holder 268 is restricted beyond this point, further motion of tab 274 away from elongated body 262 will disengage trapper 284 from knot forming device 260. Notably, even after being detached, tab 274 may remain connected to the end of non-rail portion 32 through holder 268 and trapper 284. Tension may be applied to tab 274 either manually or by releasing it so that gravity supplies the tension. Such tension is communicated to non-rail portion 32 and may also aid keeping the knot pattern properly oriented until placed and tightened.

Figure 28:
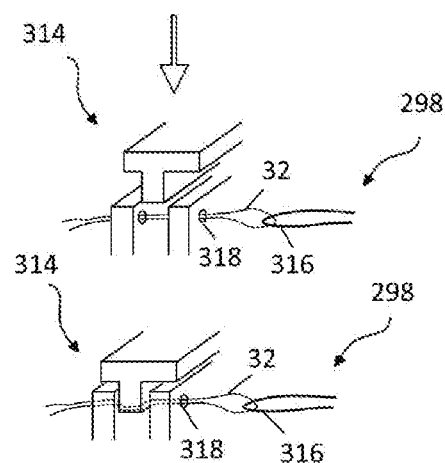

Yet another aspect of the disclosure is illustrated with respect to FIGS. 25-28, which schematically depict partial detail views of knot forming device 290, which features elongated body 292 having a first grasper 294 positioned at the distal end and rotating drum 296 for receiving holder 298 similarly configured to the above embodiments to wind around drum 296 in a knot-forming pattern. Also similar to the above embodiments, actuator 302 is slidable along elongated body 292. In this embodiment, tab 304 is detachably coupled to trapper 306, which in turn may be removably attached to housing 308 by clip 310. Tab 304 may also include projecting grasper 312, which as described above is configured to extend through the second grasper 316 of the holder 298 when wound around drum 296. Trapper 306 may include a clip 314 configured to engage and retain suture material as shown in the further detail of FIG. 28, schematically representing area A of FIG. 27. As will be appreciated, clip 314 may transition between the open configuration shown in the upper view to the closed configuration shown in the lower view. The second grasper 316 of holder 298 may be used to pull suture material, such as non-rail portion 32, through apertures 318 in clip 314. Detaching trapper 306 from housing 308 causes clip 314 to assume the closed configuration, clamping the suture to secure it. Correspondingly, trapper 306 remains connected to the end of non-rail portion 32, so that tension may be applied manually or through gravity to aid keeping the knot pattern properly oriented until placed and tightened.

Figure 29:
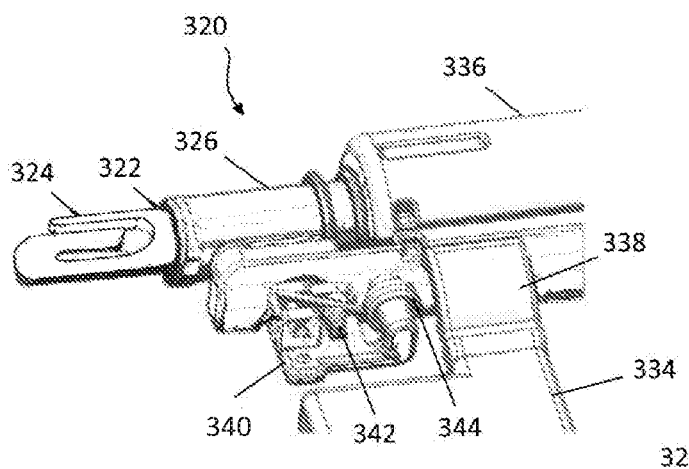
FIGS. 29-31 schematically depict an embodiment of a knot forming device with a trapper having a spring.
Figure 30:
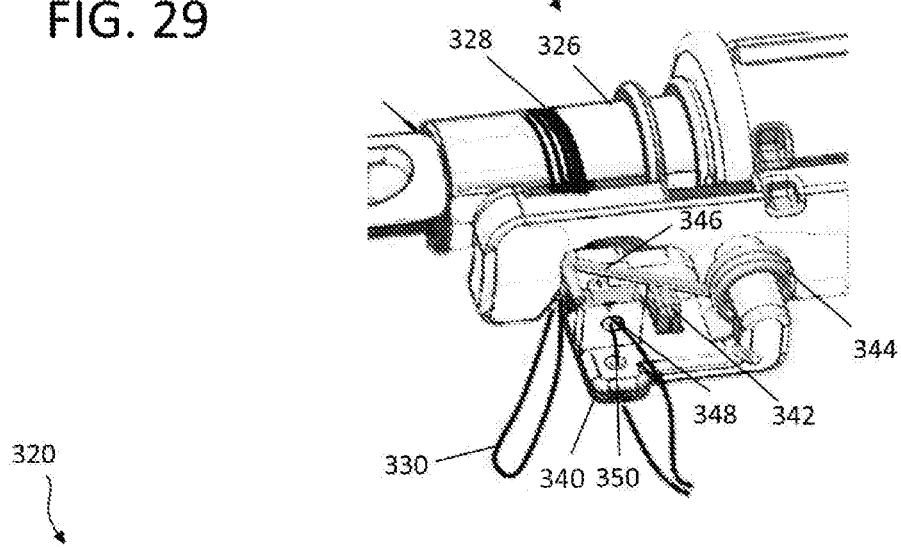
Figure 31:
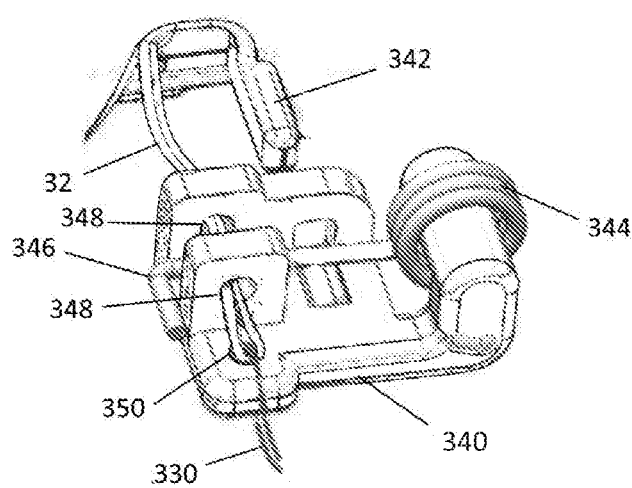

An alternative embodiment is illustrated with respect to FIGS. 29-31, which schematically depict partial detail views of knot forming device 320 and includes elongated body 322 having a first grasper 324 positioned at the distal end and rotating drum 326 for receiving holder 328 with second grasper 330 wound in a knot-forming pattern. Similarly, organizer may be employed to keep the helical windings properly oriented during the knot forming operation. Tab 334 is detachably coupled to housing 336 by clip 338, and may have other characteristics similar to those described above. Trapper 340 may be detachably coupled to actuator 332 by post 342 by spring 344. As shown more clearly in FIG. 30, spring 344 may have an arm 346 that engages post 342 when trapper 340 is attached to actuator 332, although spring 344 biases arm 346 downwards, post 342 keeps arm 346 in a raised configuration. Further, trapper 340 has a pair of aligned apertures 348 through which holder 328 may be threaded as well as an opposed aperture 350 through which one strand of holder 328 may be threaded as indicated in FIG. 30. Correspondingly, after holder 328 has been withdrawn to pull suture material, such as non-rail portion 32, into the knot-forming pattern, the second grasper 330 will engage trapper 340 at aperture 350 as shown in FIG. 31. Since non-rail portion 32 has been looped through grasper 330, after forming the knot pattern, holder 328 has pulled the suture through aligned apertures 348. After second grasper 330 has engaged aperture 350, further motion of holder 328 away from the longitudinal axis of elongated body 322 pulls trapper 340 off of post 342. Consequently, the biasing force of spring 344 causes arm 346 to assume a lowered configuration, clamping the non-rail portion 32 that has been pulled through aligned apertures 348, securing tab 334 and trapper 340 to the end of non-rail portion 32 through holder 328. Thus, as described above, tension may be applied manually or through gravity to aid keeping the knot pattern properly oriented until placed and tightened.

Figure 32:
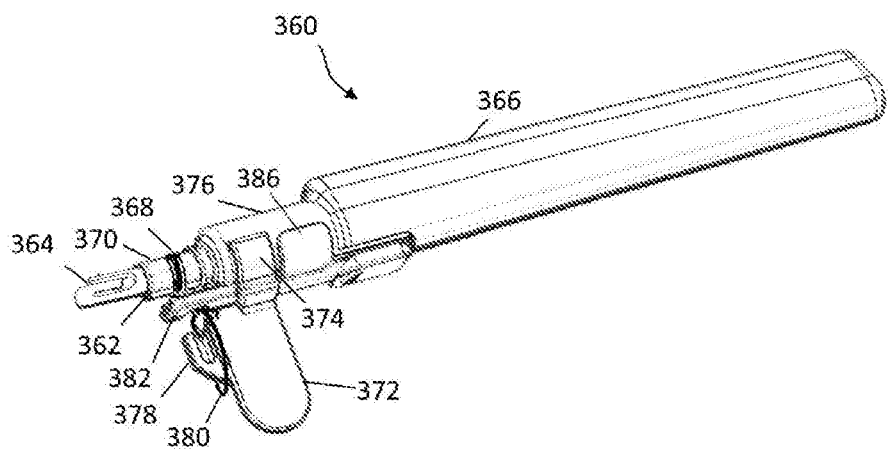
FIG. 32 depicts a schematic view of an embodiment of a knot forming device having a rotating drum coupled to a sliding actuator.
Figure 33:
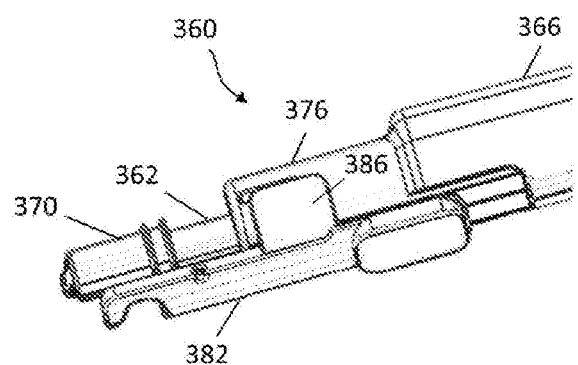
FIG. 33 depicts a schematic view of the embodiment of FIG. 32 with the actuator in a distal position.

Another aspect of this disclosure is illustrated with respect to FIGS. 32 and 33, showing knot forming device 360. As with other similar embodiments, an elongated body 362 having a first grasper 364 positioned at the distal end may extend from handle 366 as shown. Holder 368 is detachably coupled to elongated body 362, as a doubled length of wire wound around rotating drum 370 in a desired knot-forming pattern as discussed above. As noted above, rotating drum 370 may facilitate the winding of holder 368 in the knot-forming pattern, may facilitate pulling suture material to retrace the knot-forming pattern, or both. Tab 372 may be detachably coupled to knot forming device 360, such as by snapping clip 374 to housing 376. Tab 372 may also feature a protruding grasper 378 that is configured to extend through second grasper 380, formed by the loop of holder 368. As shown, knot forming device 360 also includes organizer disposed adjacent to holder 368. Drum 370 may be coupled to actuator 382, so that operation of actuator 382 also slides drum 370 coaxially over elongated body 362 in a distal direction. Correspondingly, this embodiment may be appreciated to facilitate the transfer of the helical wraps of the non-rail portion of suture material over the rail portion. As indicated by FIG. 32, when actuator 382 is in a proximal position, drum 370 is positioned proximal to first grasper 364 and when actuator 382 is in a distal position, as indicated by FIG. 33, drum 370 is coaxially disposed over first grasper 364. Therefore, the helical windings and loop formed on drum 370 may be slid smoothly onto a rail portion of the suture retained in first grasper 364 without snags or other disruptions. Further, as described above, tab 372 may restrict operation of actuator 382 when attached to knot forming device 360. For example, actuator 382 may have a plate 386 that is prevented from moving in a distal direction when clip 374 is attached to housing 376. When tab 372 is detached, plate 386 is free to move in the distal direction into the space that was occupied by clip 374.

Figure 34:
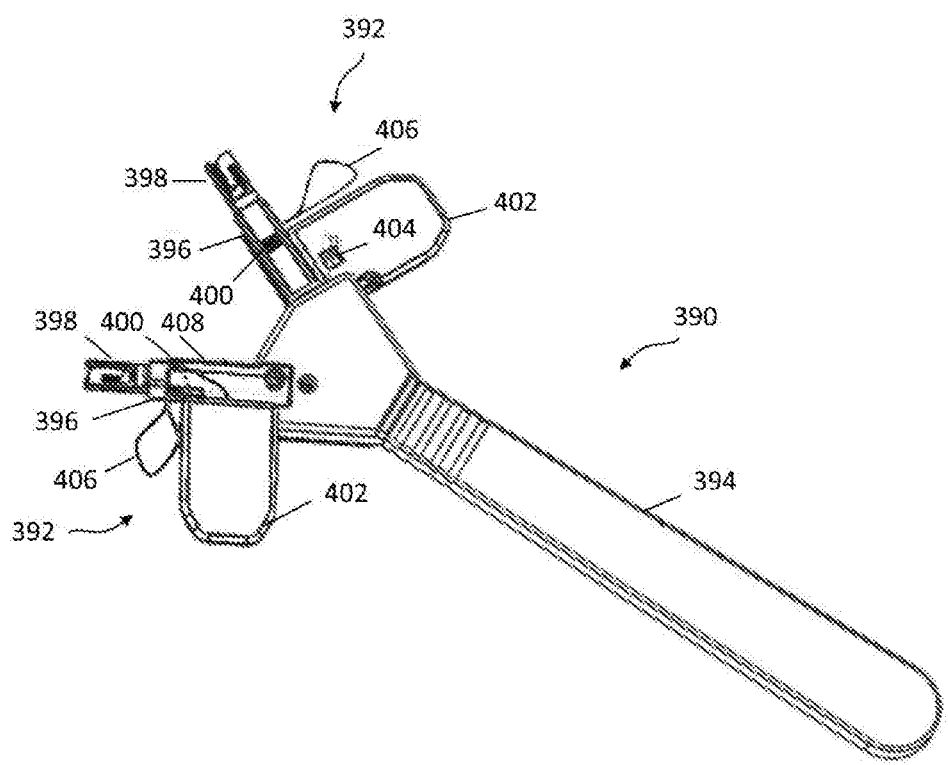
FIG. 34 depicts a schematic view of an embodiment of a knot forming device having a plurality of knot modules.

In another aspect, the techniques of this disclosure may be adapted to facilitate the formation of multiple suture knots. As shown in FIG. 34, knot forming device 390 may have a plurality of knot modules 392 projecting from handle 394, each of which is configured to form a knot in suture material according to the techniques described above. Some components of knot modules 392 may be permanently attached or integral with handle 394, or the knot modules 392 may be detachable as desired. Here, two knot modules 392 are employed but in other embodiments, any suitable number may be provided, such as three, four or more. Each knot module 392 may feature any of the components described within this disclosure to form knots in suture material. As an illustration and without limitation, each knot module 392 of this embodiment may have an elongated body 396 having a first grasper 398 positioned at the distal end. Each module 392 also has a holder 400, such as one secured by being wound around elongated body 396 in a desired pattern that will form a knot when replaced by suture material. A detachable tab 402 may be coupled to handle 394 or to a component of the knot module 392, such as elongated body 396. Each tab 402 may feature grasper 404 for releasably securing an end of holder 400 opposing the second grasper 406. Tab 402 may also have organizer 408 to provide the functionality described above for this component. In this view, only one grasper 404 and one organizer 408 are visible because knot modules 392 are attached to handle 394 in opposing orientations. During use, a knot may be formed with one of the modules 392 and then handle 394 may be rotated 180° so that the other module 392 is then presented in the same orientation. Alternatively, both knot modules 392 may be used simultaneously to tie two knots, such as in an X-shaped closure pattern. As will be appreciated, any of the components described with respect to other embodiments may be incorporated as desired, including a tensioner, a rotating drum, a trapper or others.

Described herein are certain exemplary embodiments. However, one skilled in the art that pertains to the present embodiments will understand that the principles of this disclosure can be extended easily with appropriate modifications to other applications.

What is claimed is:

1. A device for forming a knot in suture material comprising:
   an elongated body having a longitudinal axis and a first grasper configured to releasably secure suture material;
   a holder having a second grasper configured to releasably secure suture material, the holder being is detachably coupled to the elongated body proximally of the first grasper by a plurality of helical wraps of the holder around the elongated body in a knot-forming pattern with the second grasper at one end; and
   a rotating drum coaxially disposed over the elongated body, the holder being wrapped around the drum.

2. The device of claim 1, further comprising a guide at a distal end of the elongated body configured to slidably receive suture material.

3. The device of claim 1, wherein the drum further comprises a detachable tab that releasably secures an end of the holder opposing the second grasper.

4. The device of claim 1, further comprising an organizer longitudinally aligned with the elongated body and extending distally over at least a portion of the wraps of the holder.

5. The device of claim 4, further comprising a rotating drum coaxially disposed over the elongated body, wherein the drum is coupled to an actuator.

6. The device of claim 1, further comprising a tensioner looped around a portion of the holder.

7. The device of claim 1, further comprising a tab that is detachably coupled to the knot forming device that releasably secures an end of the holder opposing the second grasper.

8. The device of claim 7, wherein the tab further comprises a projecting grasper that extends in a distal direction through the second grasper.

9. The device of claim 1, further comprising a trapper that is detachably coupled to the device, wherein the trapper is configured to secure suture material when detached.

10. The device of claim 9, wherein the trapper is further configured to secure the second grasper to the suture material when detached.

11. The device of claim 1, further comprising a plurality of knot modules, wherein each knot module comprises an elongated body with a holder releasably secured by a plurality of wraps around the elongated body in a knot-forming pattern.

12. A method for forming a knot in suture material comprising:
providing a device having an elongated body with a longitudinal axis and a first grasper configured to releasably secure suture material, the device further comprising a holder having a second grasper configured to releasably secure suture material, the holder being detachably coupled to the elongated body proximally of the first grasper by a plurality of helical wraps of the holder around the elongated body in a knot-forming pattern with the second grasper at one end and a rotating drum coaxially disposed over the elongated body, the holder being wrapped around the drum;
releasably securing a rail portion of the suture material with a the first grasper;
releasably securing a non-rail portion of the suture material with the second grasper;
creating a plurality of helical windings with the non-rail portion; and
detaching the holder from the elongated body in a motion away from the longitudinal axis of the elongated body to complete the knot.

13. The method of claim 12, wherein the plurality of helical windings are created over the rail portion.

14. The method of claim 12, wherein the plurality of helical windings are created and then slid distally over the rail portion.

15. The method of claim 12, wherein the plurality of helical windings are created by driving rotation of the drum.

16. The method of claim 12, wherein creating the plurality of helical windings comprises withdrawing the holder to pull the non-rail portion into the knot-forming pattern.

17. The method of claim 16, further comprising sliding an actuator distally along the longitudinal axis of the elongated body to position the created plurality of helical windings over the rail portion.

18. The method of claim 16, further comprising looping a tensioner around a portion of the holder.

19. The method of claim 16, wherein withdrawing the holder comprises detaching a tab from the device, wherein the tab is attached to an end of the holder opposing the second grasper.

20. The method of claim 16, further comprising providing a trapper that is detachably coupled to the device, wherein the trapper secures the non-rail portion when detached.

21. The method of claim 16, wherein providing the device comprises providing a plurality of knot modules, wherein each knot module comprises an elongated body with a holder wrapped around the elongated body in a knot-forming pattern, further comprising forming a knot with each knot module.

* * * * *